(12) United States Patent
Morton

(10) Patent No.: US 8,085,897 B2
(45) Date of Patent: *Dec. 27, 2011

(54) X-RAY SCANNING SYSTEM

(75) Inventor: Edward James Morton, Guildford (GB)

(73) Assignee: Rapiscan Systems, Inc., Hawthorne, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/697,073

(22) Filed: Jan. 29, 2010

(65) Prior Publication Data

US 2010/0195788 A1    Aug. 5, 2010

Related U.S. Application Data

(63) Continuation of application No. 10/554,570, filed as application No. PCT/GB2004/001747 on Apr. 23, 2004, now Pat. No. 7,684,538.

(30) Foreign Application Priority Data

Apr. 25, 2003   (GB) .................................. 0309379.6

(51) Int. Cl.
*G01N 23/00*      (2006.01)
(52) U.S. Cl. ......................................................... 378/10
(58) Field of Classification Search ................... 378/4, 9, 378/10, 19
See application file for complete search history.

(56) References Cited

U.S. PATENT DOCUMENTS

| | | | |
|---|---|---|---|
| 2,952,790 A | 9/1960 | Steen | |
| 3,239,706 A | 3/1966 | Farrell et al. | |
| 3,768,645 A | 10/1973 | Conway et al. | |
| 4,057,725 A | 11/1977 | Wagner | |
| 4,105,922 A | 8/1978 | Lambert et al. | |
| 4,228,353 A | 10/1980 | Johnson | |
| 4,259,721 A | 3/1981 | Kuznia | |
| 4,266,425 A | 5/1981 | Allport | |
| 4,274,005 A | 6/1981 | Yamamura et al. | |
| 4,340,816 A | 7/1982 | Schott | |

(Continued)

FOREIGN PATENT DOCUMENTS

DE         2729353         1/1979

(Continued)

OTHER PUBLICATIONS

PCT Search Report, Aug. 10, 2004, Morton, Edward James et al Search Report PCT/GB2004/001729.

(Continued)

*Primary Examiner* — Jurie Yun
(74) *Attorney, Agent, or Firm* — Novel IP

(57) ABSTRACT

An X-ray scanner comprises an array (12) of X-ray detectors (16) arranged in cylindrical configuration around an imaging volume (28), and a multi-focus X-ray source (20) which extends in a helical configuration around the outside of the detector array (12). A helical gap (24) in the detector array (12) allows X-rays from the source (20) to pass through the patient (26) in the imaging volume (28), and onto the detectors (16) on the opposite side of the scanner. The source (20) is controlled so that the X-rays are produced from a number of source points along the helical locus (23) to produce a tomographic image. As the patient is stationary and the source point varied electrically, the scanning rate is sufficient to produce a series of images which can be displayed as a real time three-dimensional video image.

15 Claims, 4 Drawing Sheets

U.S. PATENT DOCUMENTS

| | | | |
|---|---|---|---|
| 4,352,021 A | 9/1982 | Boyd et al. | |
| 4,468,802 A | 8/1984 | Friedel | |
| 4,672,649 A | 6/1987 | Rutt | |
| 4,675,890 A | 6/1987 | Plessis et al. | |
| RE32,961 E | 6/1989 | Wagner | |
| 4,866,745 A | 9/1989 | Akai | |
| 4,868,856 A | 9/1989 | Frith et al. | |
| 4,887,604 A | 12/1989 | Shefer et al. | |
| 5,033,106 A | 7/1991 | Kita | |
| 5,144,191 A | 9/1992 | Jones et al. | |
| 5,247,556 A | 9/1993 | Eckert et al. | |
| 5,259,014 A | 11/1993 | Brettschneider | |
| 5,272,627 A | 12/1993 | Maschhoff et al. | |
| 5,313,511 A | 5/1994 | Annis et al. | |
| 5,367,552 A | 11/1994 | Peschmann | |
| 5,412,702 A | 5/1995 | Sata | |
| 5,467,377 A | 11/1995 | Dawson | |
| 5,511,104 A | 4/1996 | Mueller et al. | |
| 5,604,778 A | 2/1997 | Polacin et al. | |
| 5,633,907 A | 5/1997 | Gravelle et al. | |
| 5,661,774 A | 8/1997 | Gordon et al. | |
| 5,689,541 A | 11/1997 | Schardt | |
| 5,796,802 A | 8/1998 | Gordon | |
| 5,818,897 A | 10/1998 | Gordon | |
| 5,841,831 A | 11/1998 | Hell et al. | |
| 5,859,891 A | 1/1999 | Hibbard | |
| 5,881,122 A | 3/1999 | Crawford et al. | |
| 5,887,047 A | 3/1999 | Bailey et al. | |
| 5,901,198 A | 5/1999 | Crawford et al. | |
| 5,909,477 A | 6/1999 | Crawford et al. | |
| 5,966,422 A | 10/1999 | Dafni et al. | |
| 5,974,111 A | 10/1999 | Krug et al. | |
| 5,982,843 A | 11/1999 | Bailey et al. | |
| 5,987,097 A | 11/1999 | Salasoo | |
| 6,018,562 A | 1/2000 | Willson | |
| 6,026,171 A | 2/2000 | Hiraoglu et al. | |
| 6,035,014 A | 3/2000 | Hiraoglu et al. | |
| 6,067,366 A | 5/2000 | Simanovsky et al. | |
| 6,075,871 A | 6/2000 | Simanovsky et al. | |
| 6,076,400 A | 6/2000 | Bechwati et al. | |
| 6,078,642 A | 6/2000 | Simanovsky et al. | |
| 6,091,795 A | 7/2000 | Schafer et al. | |
| 6,122,343 A | 9/2000 | Pidcock | |
| 6,149,592 A | 11/2000 | Yanof et al. | |
| 6,181,765 B1 | 1/2001 | Sribar et al. | |
| 6,183,139 B1 | 2/2001 | Solomon et al. | |
| 6,218,943 B1 | 4/2001 | Ellenbogen | |
| 6,236,709 B1 | 5/2001 | Perry et al. | |
| 6,269,142 B1 | 7/2001 | Smith | |
| 6,324,249 B1 | 11/2001 | Fazzio | |
| 6,546,072 B1 | 4/2003 | Chalmers | |
| 6,661,866 B1 * | 12/2003 | Limkeman et al. | 378/19 |
| 6,735,271 B1 | 5/2004 | Rand et al. | |
| 6,760,407 B2 | 7/2004 | Price et al. | |
| 6,920,196 B2 * | 7/2005 | Ueno et al. | 378/19 |
| 6,993,115 B2 | 1/2006 | McGuire et al. | |
| 7,333,588 B2 | 2/2008 | Mistretta et al. | |
| 7,684,538 B2 * | 3/2010 | Morton et al. | 378/10 |
| 2001/0022346 A1 | 9/2001 | Katagami et al. | |
| 2001/0033635 A1 | 10/2001 | Kuwabara | |
| 2002/0031202 A1 | 3/2002 | Callerame et al. | |
| 2002/0094064 A1 | 7/2002 | Zhou et al. | |
| 2002/0176531 A1 | 11/2002 | McClelland et al. | |
| 2003/0021377 A1 | 1/2003 | Turner et al. | |
| 2003/0031352 A1 | 2/2003 | Nelson et al. | |
| 2004/0120454 A1 | 6/2004 | Ellenbogen et al. | |
| 2004/0213379 A1 | 10/2004 | Bittl | |
| 2004/0252807 A1 | 12/2004 | Skatter et al. | |
| 2004/0258305 A1 | 12/2004 | Burnham et al. | |
| 2005/0031075 A1 | 2/2005 | Hopkins et al. | |
| 2005/0053189 A1 | 3/2005 | Gohno et al. | |
| 2005/0105682 A1 | 5/2005 | Heumann et al. | |
| 2005/0111610 A1 | 5/2005 | De Man et al. | |
| 2005/0157925 A1 | 7/2005 | Lorenz | |

FOREIGN PATENT DOCUMENTS

| | | |
|---|---|---|
| EP | 0 432 568 | 6/1991 |
| EP | 0 531 993 | 3/1993 |
| EP | 0 584 871 | 3/1994 |
| EP | 0 924 742 | 6/1999 |
| EP | 0 930 046 | 7/1999 |
| EP | 1 277 439 | 1/2003 |
| EP | 1374776 | 1/2004 |
| EP | 1558142 | 8/2005 |
| FR | 2328280 | 5/1977 |
| GB | 1497396 | 1/1978 |
| GB | 1526041 | 9/1978 |
| GB | 2 015 245 | 9/1979 |
| GB | 2089109 | 6/1982 |
| GB | 2 212 903 | 8/1989 |
| GB | 2437777 | 11/2007 |
| JP | 570175247 | 10/1982 |
| JP | 590016254 | 1/1984 |
| JP | 59075549 | 4/1984 |
| JP | 60 0015546 | 1/1985 |
| JP | 60 0021440 | 2/1985 |
| JP | 2004 079128 | 3/1992 |
| JP | 060038957 | 2/1994 |
| JP | 10 211196 | 8/1998 |
| JP | 2001 176408 | 6/2001 |
| JP | 2003126075 | 5/2003 |
| JP | 2004000605 | 1/2004 |
| JP | 2005013768 | 1/2005 |
| WO | WO 95/28715 | 10/1995 |
| WO | WO 99/60387 | 11/1999 |
| WO | WO 03/051201 | 6/2003 |
| WO | WO 03/105159 | 12/2003 |
| WO | WO 2004/111625 | 12/2004 |
| WO | WO 2005/084351 | 9/2005 |
| WO | WO 2006/135586 | 12/2006 |
| WO | WO 2007/076707 | 7/2007 |
| WO | WO 2007/079675 | 7/2007 |

OTHER PUBLICATIONS

PCT Search Report, Aug. 10, 2004, Morton, Edward James et al Search Report PCT/GB2004/001747.

US 5,987,079, 11/1999, Scott et al. (withdrawn)

* cited by examiner

X-RAY SCANNING SYSTEM

CROSS REFERENCE

The present application is a continuation of U.S patent application Ser. No. 10/554,570 filed Mar. 16, 2007, issued as U.S. Pat. No. 7,684,538, which is a national stage application of PCT/GB2004/001747, filed on Apr. 23, 2004 and which calls to Great Britain Patent Application Number 0309379.6, filed on Apr. 25, 2003, for priority.

The present invention relates to X-ray scanning. It has particular application in medical computed tomography (CT) scanning, although it could equally be used in other suitable applications.

X-ray computed tomography scanners have been used in medical imaging for many years. A conventional system comprises an X-ray tube that is rotated about an axis with an arcuate X-ray detector array also rotated at the same speed around the same axis. The patient is placed with their centre of gravity close to the axis of rotation, and moved along the axis as the tube is rotated. A fan-beam of X-radiation passes from the source through the patient to the X-ray detector array.

The X-ray detector array records the intensity of X-rays passed through the patient at each location along its length. From these recorded X-ray intensities, it is possible to form a tomographic (cross-sectional) image, typically by means of a filtered back projection algorithm, if one set of projection data is recorded at each source angle. In order to produce an accurate tomographic image of an object, such as a part of the patient, it can be shown to be a requirement that the X-ray source pass through every plane through the object. In the arrangement described above, this is achieved by the rotational scanning of the X-ray source and the longitudinal movement of the patient.

In this type of system the rate at which X-ray tomographic scans can be collected is dependent on the speed of rotation of the gantry that holds the X-ray source and detector array. In a modern medical gantry, the entire tube-detector assembly and gantry will complete two revolutions per second. This allows up to four tomographic scans to be collected per second.

As the state-of-the-art has developed, the single ring of X-ray detectors has been replaced by multiple rings of X-ray detectors. This allows many slices (typically up to 8) to be scanned simultaneously and reconstructed using filtered back projection methods adapted from the single scan machines. In a further improvement of this process, the patient position may be moved along the axis of the scanner such that the source describes a helical motion about the patient. This allows a more sophisticated cone beam image reconstruction method to be applied that can in principle offer a more accurate volume image reconstruction. The combination of physical motion of the patient and source rotation about the patient when combined with multiple ring X-ray detectors allows volume images of the patient to be obtained over a period of several seconds.

In a further development, swept electron beam scanners have been demonstrated whereby the mechanical scanning motion of the X-ray source and X-ray detectors is eliminated, being replaced by a continuous ring (or rings) of X-ray detectors that surrounds the patient with a moving X-ray source being generated as a result of sweeping an electron beam around an arcuate, anode. This allows images to be obtained more rapidly than in conventional scanners. By simultaneous movement of the patient along the axis of the scanner, volume image data may be acquired in timescales of the order of a second.

The present invention provides an X-ray imaging system comprising a multi-focus X-ray source extending around an imaging volume to be imaged by the system, and defining a locus of source points from which X-rays can be directed through the imaging volume, and an X-ray detector array also extending around the imaging volume and arranged to detect X-rays from the source points which have passed through the imaging volume, wherein the source points are arranged to follow a three-dimensional locus around the imaging volume such that data from the detector array can be used to produce a three dimensional tomographic image of a stationary object within the imaging volume.

Preferably the detector array is substantially cylindrical and said locus covers at least half of the circumference of the cylinder, more preferably the full circumference, and substantially the whole of the length of the cylinder. More preferably the locus is substantially helical.

However, it will be appreciated that other locus configurations could equally be used which would enable the object in the imaging volume to be fully tomographically imaged. Preferably the locus passes through substantially every plane which passes through the imaging volume.

The system preferably further comprises control means arranged to scan the imaging volume by activating each of the X-ray source points and collecting respective image data sets, and imaging means arranged to produce a three-dimensional image of the imaging volume from the data sets. Preferably the control means is arranged to scan the imaging volume repeatedly to produce consecutive images of the imaged volume. Still more preferably the system further comprises display means arranged to display the consecutive images to produce a real-time video image of the imaged volume.

Preferably the control means is further arranged to activate one of the source points to produce a plane image of an object and to store the plane image for display. More preferably the control means is arranged to activate said one of the source points repeatedly thereby to produce a series of plane images, and to display the plane images in sequence to produce a plane video image. Still more preferably the control means is arranged to alternate between a first mode in which it produces a plane image data set and a second mode in which it produces a tomographic image data set, and to process the data sets to produce a combined image data set for producing a combined display.

The plane image may comprise a fluoroscopic image. Such plane images, especially when used to generate a real time video image, are used for a variety of purposes, including the monitoring of medical operations where the position of instruments such as catheters inside a patient can be monitored in real time Indeed the present invention further provides an X-ray imaging system comprising an X-ray source defining plurality of source points around an imaging volume from which X-rays can be directed through the imaging volume, and an X-ray detector array extending around the imaging volume and arranged to detect X-rays from the source points which have passed through the imaging volume, and control means arranged to alternate between a first mode in which it controls the source to produce X-rays from one of the source points to produce a plane image data set and a second mode in which it controls the source to produce X-rays from each of the source points to produce a tomographic image data set, and to process the data sets to produce a combined image data set for producing a combined display.

Rather than producing just one plane image, a plurality of source points can be used to produce a plurality of plane images in different planes.

The control means may arranged to activate a further one of source points close to said one of the source points whereby a pair of data sets are produced, and to combine the data sets so that the plane image or each of the plane images is a stereo image.

Preferably the control means is arranged to process the data sets by mapping features from one of the data sets onto the other of the data sets thereby to enhance the image produced from said other of the data sets.

Preferred embodiments of the present invention will now be described by way of example only with reference to the accompanying drawings in which.

Figure 1:
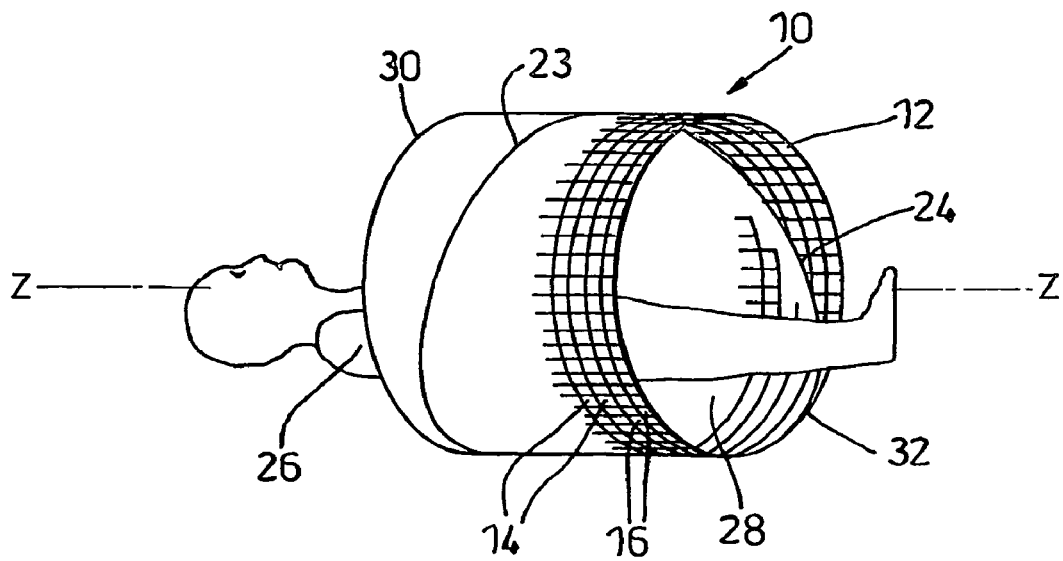
FIG. 1 is a schematic perspective view of an X-ray scanner according to a first embodiment of the invention.

Referring to FIG. 1, an X-ray scanner 10 comprises a cylindrical multi-element detector array 12 formed from many hundred individual rings 14 of detector elements 16. Each ring 14 may typically be of width 1-3 mm with centre-to-centre spacing between individual detector elements in the ring of 1-3 mm. The diameter of the detector array 12 is typically in the range 60-80 cm. The individual detector elements 16 should preferably have good efficiency at detecting X-rays and can be manufactured, for example, from high density scintillators, semiconductor materials or pressurised gas ionisation chambers. The detector array 12 has a longitudinal central axis Z, and is arranged to enable a patient 18 to be placed inside the array 12 approximately on the central axis Z.

Figure 2:
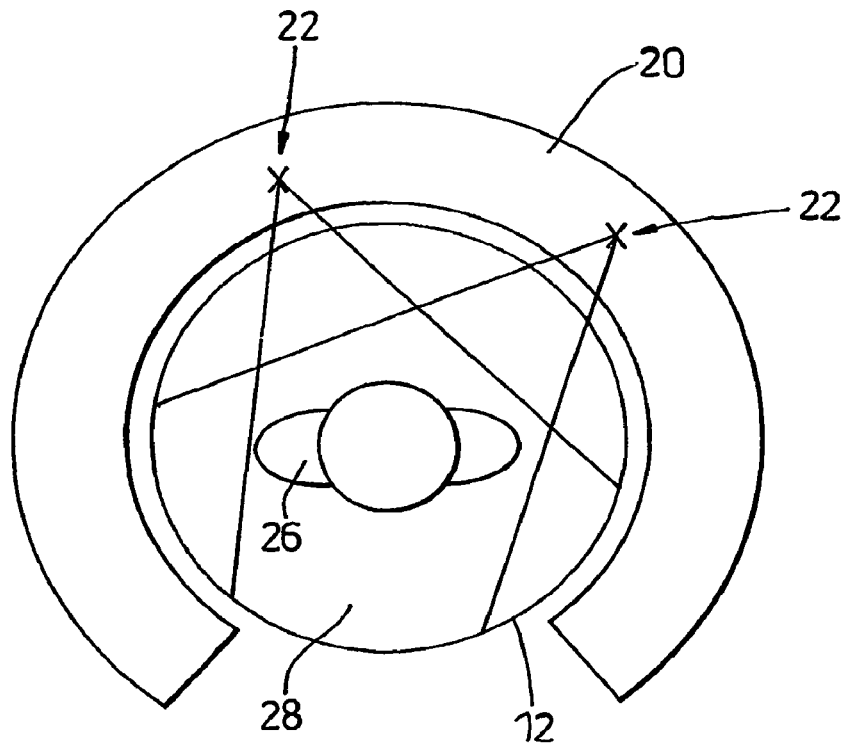
FIG. 2 is a cross section through the scanner of FIG. 1.

A multi focus X-ray source 20 is wrapped around the outside of the X-ray sensor array 12 in a helical manner as shown in FIG. 2. The source 20 allows X-rays to be emitted from each of a number of source points 22 spaced along the source 20. X-rays from the multi focus X-ray source 20 pass through a clear helical slot 24 that is present in the detector array 12 and aligned with the source points 22 such that, for each source point 22, the X-rays irradiate a group of the X-ray detector elements 16 on the opposite side of the detector array 12.

The slot 24 in the detector array 12 is cut in a way that leads to the locus 23 of source points 22 as shown in FIG. 1. This helical slot 24, and the resulting helical source trajectory, means that the set of data collected following X-ray transmission through the patient 26 is mathematically sufficient to form a true three dimensional image reconstruction. This is because the locus 23 of source points 22 passes through every plane passing through the scanning volume 28 which is essentially defined as the volume within the sensor array 12, i.e. radially inside the array 12 and between its two longitudinal ends 30, 32.

The multi-focus X-ray source 20 comprises a continuous anode held at a high positive potential with respect to a plurality of grid controlled electron emitters. Each emitter is "turned on" in turn and the corresponding electron beam irradiates the target, so producing X-radiation from a respective source point 22. By changing the active grid controlled electron emitter, the effect of moving the X-ray source around the patient can be obtained. The X-ray source 20 is housed in a thick housing to avoid irradiating X-ray detectors 16 and other components in the system close to the X-ray source 20. An example of a suitable source is described in our co-pending UK patent application No. 0309383.8 X-Ray Tube Electron Sources.

Collimation of the X-rays from the source 20 is important to minimise radiation dose to the patient 26. The source 20 therefore includes collimators arranged to restrict X-ray beams to only that part of the patient 26 that lies directly between the source and corresponding detectors. Some suitable collimation systems are disclosed in our co-pending UK patent application No. 0309374.7 entitled X-Ray Sources, and also in UK patent application No. 0216891.2 entitled Radiation Collimation.

To form an image of the patient 26, the patient is placed in position with the part of their body to imaged within the scanning volume 28. Then, with the patient 26 being kept stationary, each of the X-ray source points 22 is operated in turn to scan the patient, and for each source point 22 data from the group of detector elements 16 opposite the source point 22 is used to form an image frame. All of the image frames produced in one scan are then processed to form a three-dimensional tomographic X-ray image of the patient as will be described in more detail below.

Figure 3:
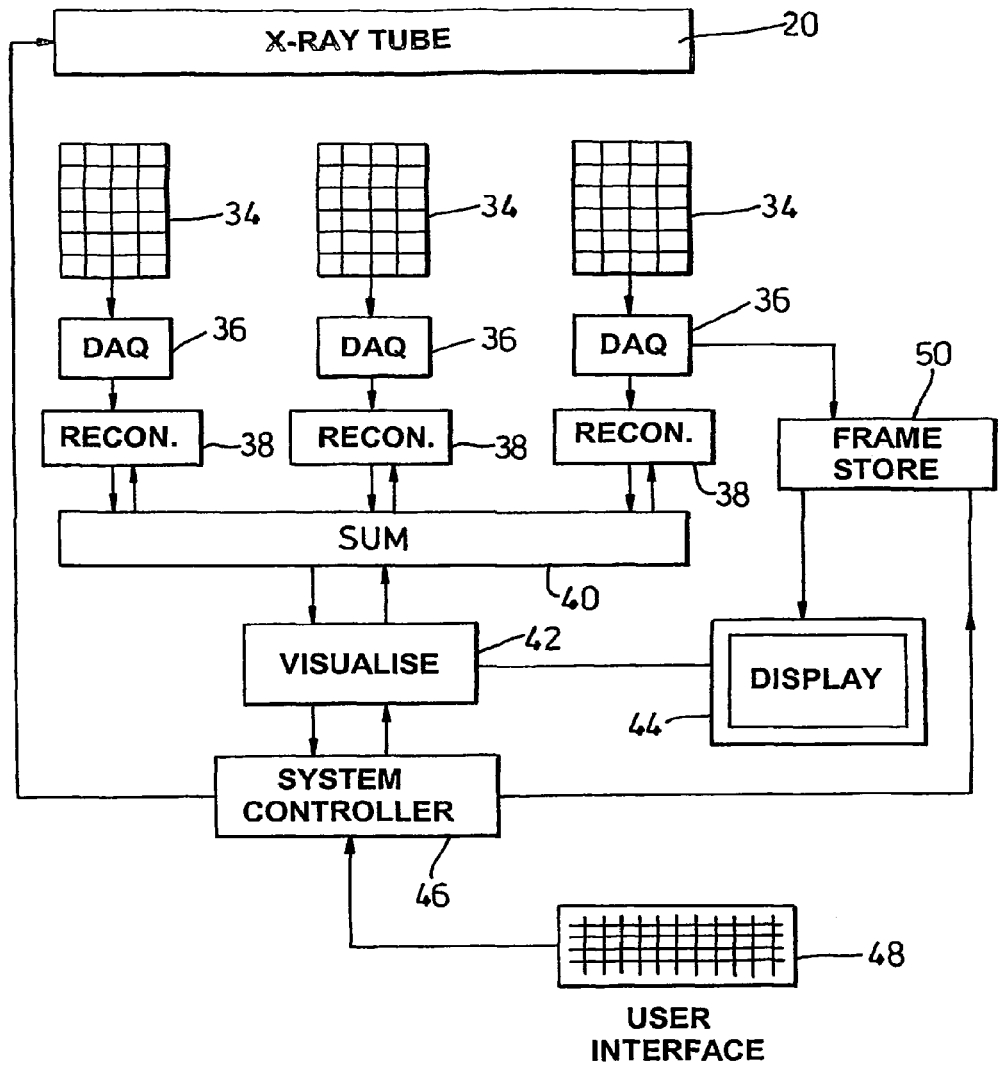
FIG. 3 is a system diagram of a scanner system including the scanner of FIG. 1.

Referring to FIG. 3, the complete X-ray system comprises the multi-focus X-ray tube 22 and detector array 12, which is made up of a number of sensor blocks 34. Each sensor block comprises an array of detecting elements 16, typically 8×4 or 16×8 pixels, that are electronically coupled to suitable amplifiers, sample-and-hold amplifiers, analogue multiplexor and analogue-to-digital converter. Each sensor block 34 is connected to a respective data acquisition circuit (DAQ) 36 that provides gain and offset correction and, where appropriate, linearization for input to the image reconstruction process. To cope with the high data rates generated by the detector array 12, multiple hardwired image reconstruction circuits 38 are used to process data in parallel from the DAQ circuits 36. The image reconstruction circuits are connected via a summing circuit 40 to visualisation circuit 42, which in turn is connected to a display 44. A system controller 46 is connected to, and controls operation of, the X-ray tube 20 and the detector bocks 34 and other circuits 36, 38, 40, 42 and display 44. A user interface 48, which can include, for example, a keyboard, a hand held controller, and action specific control buttons, is connected to the controller 46 to allow a user to control operation of the system.

During each scan the X-ray tube 20 is controlled so that each of the source points 22 produces a beam of X-rays in turn. The order of activation of the source points 22 can be sequential, or can be ordered so as to reduce the thermal load on the tube anode, as described in our co-pending UK patent application No. 0309387.9 entitled X-ray Scanning. For each scan, data from each of the detector blocks 34 is processed in the respective DAQ 36 and image reconstruction circuit 38. The reconstructed images from each reconstruction circuit 38 are summed and passed to a visualisation unit 42 that creates a 3D tomographic image. The images from subsequent scans are combined to form a real time 3D video image which is shown in the display 44.

For equivalent image quality, the faster the scan time, the higher the X-ray tube current. For example, a 5 ms scan time requires an anode current in excess of 500 mA for high quality medical diagnostic imaging.

It will be appreciated that the combination of a helical trajectory multi-focus X-tray tube 20 and multi-ring X-ray detector 12 with helical slot 24 allows true full volume tomographic image data to be collected with no mechanical movement of X-ray source, X-ray detector or patient. Since no mechanical movement is involved, it is possible to generate volume images very quickly, with the only limitation being the output power of the X-ray tube. The scanner described can therefore provide full three-dimensional X-ray tomographic scans using accurate cone-beam three dimensional reconstruction algorithms over millisecond timescales.

Applications for the scanner in this mode of operation include volume cardiac imaging (single cycle) where movies of cardiac motion can be generated over a single cycle. Assume a cardiac cycle time of 800 ms and a 4 ms tomographic scan time, a single cardiac cycle movie will contain 200 volume tomographic images. A preferred use of this scanner is in cardiac angiography in which iodine contrast agent is passed through the heart and surrounding vessels.

Figure 4:
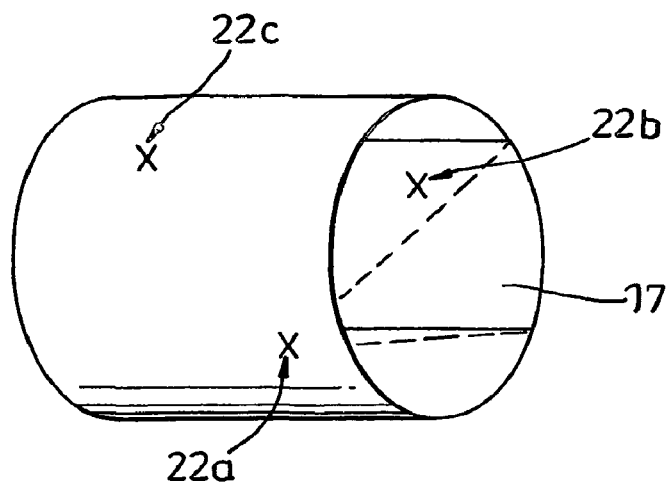
FIG. 4 is a schematic perspective view of the scanner of FIG. 1 reconfigured according to a second embodiment of the invention.

Referring to FIG. 4, in a second mode of operation, the scanner system of FIGS. 1 to 3 is set up for use in fluoroscopy. This can be single plane, bi-plane or multi-plane fluoroscopy. For single plane fluoroscopy a single source point 22a is used, and a beam of X-rays passed from that source point 22a, through the patient, and onto a group 17 of the detector elements 16. The data from the detector elements 16 is used to form an image frame data set which represents a 2 dimensional X-ray projection image of the imaged volume. This process is repeated in successive imaging periods, which may be of the order of 5 ms. It will be appreciated that this is significantly faster than conventional fluoroscopy for which the corresponding period is of the order of 40 ms or more. In this case the image frame data sets are output directly from the DAQs 36 to a frame store 50 from which they can be displayed in turn as images on the display 44 to provide a real time 2D video image of the patient.

Since a large number of X-ray source points 22 are present in the system, it can easily be controlled to alternate between two, three or more source points 22b, 22c spaced around the patient. For each source point 22a 22b, 22c, a corresponding group of detector elements 16 will be used to produce a respective series of fluoroscopic image frames. By cycling between the source points 22a, 22b, 22c simultaneous video images in a number of planes can be produced. These fluoroscopic images can either simply be displayed simultaneously on the display 44 or processed to provide a single video image combining features from each of the plane video images. The angle between planes may be adjusted electronically by switching the location of the emitting electron source. Applications for the system used in this mode are neuroradiology and neuroangiography.

The fluoroscopic images produced can be improved by using the methods described in UK patent application No. 0216893.8 entitled Image Colouring and UK patent application No. 0216889.6 entitled Image Control.

Figure 5:
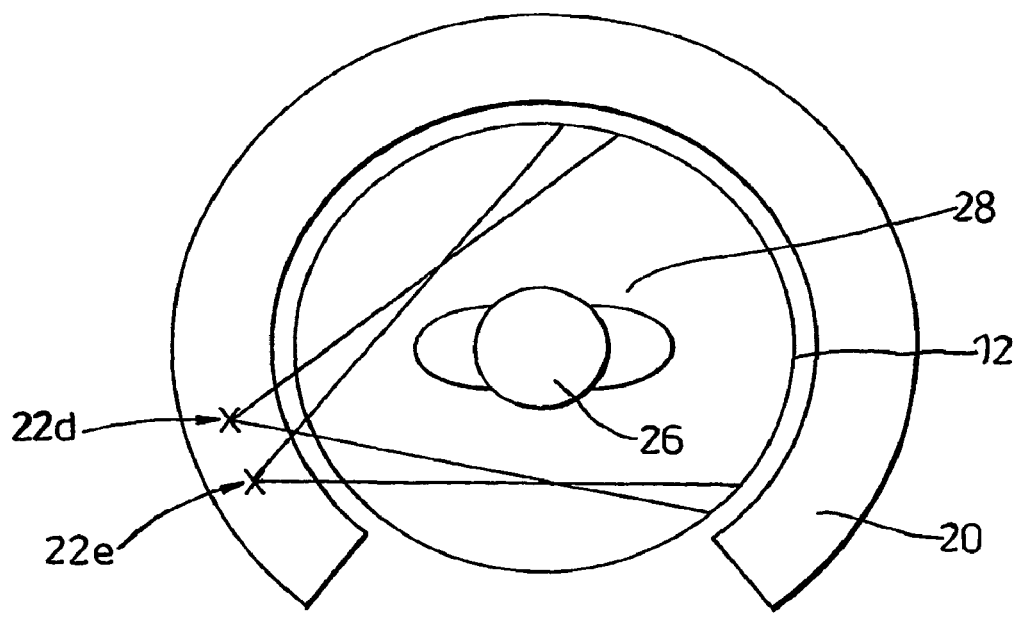
FIG. 5 is a cross section through the scanner of FIG. 1 reconfigured according to a third embodiment of the invention.

Referring to FIG. 5, in a further mode of operation, the system is set up to provide stereo imaging of the imaging volume 28. In this set-up, two source points 22d, 22e are used which are close together. Each of them is activated in turn to produce a respective transmission image data set from a corresponding group of detector elements 16 on the opposite side of the imaging volume 28. These image data sets are stored in the frame store 50. A pair of image frame data sets, one from each source point 22d, 22e, is combined to produce a stereo image data set representing an image of the imaged volume, and successive stereo images can be displayed to produce a real time stereo view video image of the imaged volume 28. The angle between the two sources 22d, 22e, and hence the degree of parallax, can be adjusted dynamically to suit the size of the patient or organ being imaged.

Because the source points 22 to be used, and the order in which they are used, can be controlled by the controller 46 in any suitable order or combination, it is also possible for the scanner to switch rapidly between any of the three modes of operation described above. This will reduce the rate at which data can be collected for each mode, but enables the images produced in each mode to be combined. For example in one mode the scanner is arranged to scan the object repeatedly to produce a 3D tomographic image of the object, but, between each successive pair of scans, to use one of the source points 22 to produce a 2D flouroscopic image of the object. The tomographic image is then analysed by the visualising unit 42 to identify specific features, which are then identified with corresponding features on the fluoroscopic image. The fluoroscopic image is then enhanced by mapping features from the 3D image onto the 2D image using software pointers to show the mapped features more clearly. This can be advantageous, for example where one or more features is obscured in the 2D image, or where two or more features cannot be distinguished from each other. Alternatively, features identified in the fluoroscopic image can be mapped directly onto the three-dimensional tomographic image. It will be appreciated that the automatic registration of the fluoroscopic image and volume tomographic data can be of major clinical advantage.

Similar combinations can be made of the stereo view imaging data and the tomographic imaging data, or indeed of all three imaging methods. The combination of volume real-time tomographic imaging, real-time multi-plane fluoroscopy and real-time stereo view imaging in one spatially registered imaging system can lead to shortening of clinical procedures, enhanced diagnosis and, in some cases, a lowering of patient dose.

Figure 6:
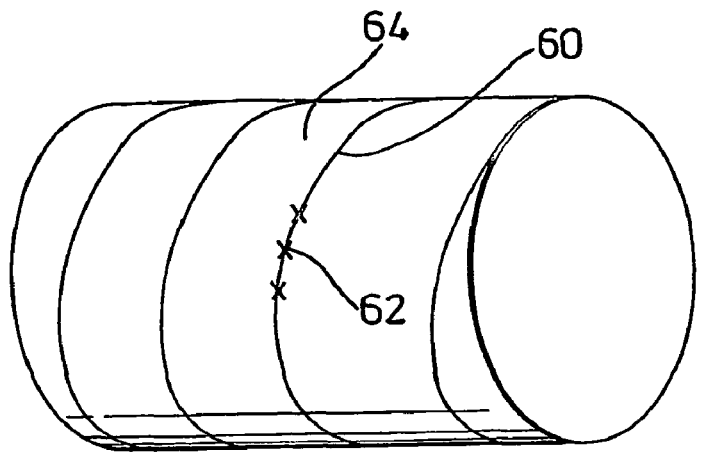
FIG. 6 is a schematic perspective view of an X-ray scanner according to a second embodiment of the invention.
Figure 7:
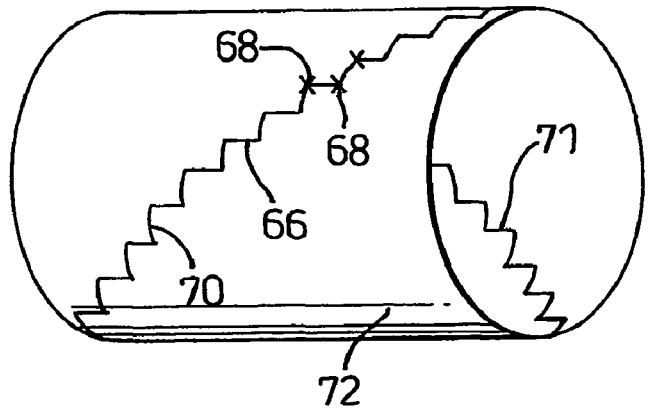
FIG. 7 is a schematic perspective view of an X-ray scanner according to a third embodiment of the invention.
Figure 8:
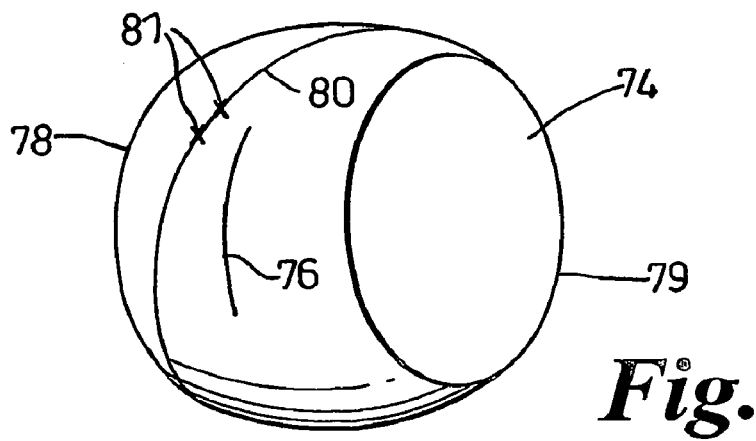
FIG. 8 is a schematic perspective view of an X-ray scanner according to a fourth embodiment of the invention.

It will be appreciated that the exact shape of the X-ray source can be modified substantially. The embodiment described above is the simplest to use in many circumstances as the regular helix with a single turn produces data which is simple to analyse. However, other shapes of source could be used. For example, referring to FIG. 6, in a second embodiment of the invention, a helical locus 60 of X-ray source points 62 is again used, but in this case the helix has a plurality of turns around the detector array 64. Referring to FIG. 7, in a fourth embodiment, the locus 66 of source points 68 is not in a helix, but is made up of two stepped loci 70, 71 each extending halfway round the circumference of the cylindrical detector array 72 and along its full length. Finally, referring to FIG. 8, in a fourth embodiment the detector array 74 is not straight cylindrical, but instead is part spherical being of larger circumference at its centre line 76 than at its longitudinal ends 78, 79. The locus 80 of source points 81 extends from one end 78 of the detector array 74 to the other 79 while following a single turn around its circumference.

The invention claimed is:
1. An X-ray imaging system for generating a three-dimensional image of an object that is positioned within an imaging volume having a central axis defined by a length comprising:
 a detector array comprising a plurality of rings of detector elements, wherein each of said plurality of rings encompasses a portion of said imaging volume, each of said plurality of rings has a length parallel to said central axis, and the length of the central axis is greater than the length of each one of said plurality of rings; and a stationary X-ray source comprising an anode with more than one source point, wherein the more than one source point are positioned behind said detector array relative to the imaging volume, wherein said detector elements detect X-rays which are from the more than one source point and which have passed through at least one slot in said detector array and into the imaging volume, wherein data from the detector array is used to produce said three dimensional image of said object within the imaging volume, and wherein a three dimensional image of the entire imaging volume is obtained without moving said object.

2. The system of claim 1 wherein the detector array is substantially cylindrical.

3. The system of claim 1, wherein said at least one slot in said detector array extends along at least a portion of a length of said detector array.

4. The system of claim 3, wherein each of said more than one source point are aligned with said slot.

5. The system of claim 1, wherein the source points are arranged to follow a three-dimensional locus around the imaging volume.

6. The system of claim 5, wherein the locus passes through substantially every plane of the imaging volume.

7. The system of claim 1, further comprising a controller for scanning the imaging volume by activating each of the source points.

8. The system of claim 7, wherein said controller causes image data sets to be collected.

9. The system of claim 8, wherein said controller causes said three-dimensional image to be produced from the data sets.

10. The system of claim 7, wherein the controller scans the imaging volume repeatedly to produce consecutive images.

11. The system of claim 10, further comprising a display for displaying the consecutive images to produce a real-time video image.

12. The system of claim 7, wherein the controller activates one of the source points to produce a planar image of the object and to store the planar image for display.

13. The system of claim 1 further comprising a controller, wherein the controller activates one of the source points repeatedly to produce a series of planar images and displays the planar images in sequence to produce a planar video image.

14. The system of claim 1, wherein a controller alternates between a first mode in which it produces a planar image data set and a second mode in which it produces a tomographic image data set.

15. The system of claim 14, wherein the controller subsequently processes the data sets to produce a combined image data set.

* * * * *